United States Patent [19]

Post et al.

[11] Patent Number: 5,275,934
[45] Date of Patent: Jan. 4, 1994

[54] METHOD OF DETECTING VIRAL INFECTION IN VACCINATED ANIMALS

[75] Inventors: Leonard E. Post, Ann Arbor; Darrell R. Thomsen, Kalamazoo, both of Mich.

[73] Assignee: The Upjohn Company, Kalamazoo, Mich.

[21] Appl. No.: 848,640

[22] Filed: Mar. 9, 1992

Related U.S. Application Data

[60] Division of Ser. No. 318,719, Feb. 9, 1989, Pat. No. 5,128,128, which is a division of Ser. No. 049,865, Mar. 27, 1987, Pat. No. 4,810,634, which is a continuation-in-part of Ser. No. 760,130, Jul. 29, 1985, abandoned.

[51] Int. Cl.$^5$ ............... G01N 33/569; G01N 33/543; A61K 39/245
[52] U.S. Cl. ........................................ 435/5; 435/7.1; 435/7.92; 424/89
[58] Field of Search ................ 435/7.1, 7.92, 5; 424/89

[56] References Cited

U.S. PATENT DOCUMENTS

| | | | |
|---|---|---|---|
| 4,514,497 | 4/1985 | Kit et al. | 435/235.1 |
| 4,609,548 | 9/1986 | Kit et al. | 424/89 |
| 4,680,176 | 7/1987 | Berns et al. | 435/235.1 |
| 4,711,850 | 12/1987 | Kit et al. | 435/235.1 |
| 4,810,634 | 3/1989 | Post et al. | 435/235 |
| 5,047,237 | 9/1991 | Cochran | 424/89 |

FOREIGN PATENT DOCUMENTS

| | | |
|---|---|---|
| 0074808 | 3/1983 | European Pat. Off. |
| 0083286 | 7/1983 | European Pat. Off. |
| 0133200 | 2/1985 | European Pat. Off. |
| 0141458 | 5/1985 | European Pat. Off. |
| 0162738 | 11/1985 | European Pat. Off. |

OTHER PUBLICATIONS

H. Hampl, et al., "Characterization of the Envelope Proteins of Pseudorabies Virus", J. Virol., 52(2), pp. 583-90 (1984).

T. Ben-Porat and A. S. Kaplan, "Molecular Biology of Pseudorabies Virus", in B. Roizman ed., The Herpesviruses, 3, pp. 105-73 (1984).

A. K. Robbins, et al., "Localization of a Pseudorabies Virus Glycoprotein Gene Using an *E. coli* Expression Plasmid Library", in Herpesvirus, pp. 551-61 (1984).

Wathen, L. M. K., et al., "Production and Characterization of Monoclonal antibodies Directed Against Pseudorabies Virus", 1985, Virus Research 4:19-29.

Stevely, J. Virol. 16(5):944-950 (Oct. 1975).

Pouwels et al., (1985) in Cloning Vectors, (Elsevier Science Publishers, Amsterdam), pp. I-1, I-3, I-4, I-5, I-7, I-8, V-1, V-I-1, VI-2, VIII-1, VIII-2, VIII-3, VIII-B-b-i-8, VII-1, VII-2.

Robbins et al., J. Virol. 59(3), 635-45, (Sep. 1986).

D. P. Gustafson, "Pseudorabies", in Diseases of Swine, 5th ed., A. D. Leman et al., 209-23 (1981).

Jones, T. C. and R. D. Hunt, "Pseudorabies (Infectious Bulbar Paralysis, Aujeszky's Disease, Mad Itch) in Veterinary Pathology", 5th Ed., Lea & Febiger, 322-26(1983).

C. E. Aronson, "Pseudo-Cine ™ with Havlogen ®", Veterinary Pharmaceuticals & Biologicals 15/90 (1982-1983).

C. E. Aronson, "PR-VAC®", and PR-VAC-®-Killed, and PR-VAC®/Leptoferm-5, Veterinary Pharmaceuticals & Biologicals 15/98-99(1982-1983).

Ben-Porat, T. and A. S. Kaplan, "Synthesis of Proteins in Cells Infected with Herpesvirus V. Viral Glycoproteins", Virology 41:265-73(1970).

Kaplan, A. S. and T. Ben-Porat, "Synthesis of Proteins in Cells Infected with Herpesvirus, VI. Characterization of the Proteins of the Viral Membrane", Proc. of Natn'l Acad. of Sciences 66(3):799-806(1970).

(List continued on next page.)

Primary Examiner—Richard A. Schwartz
Assistant Examiner—Philip W. Carter
Attorney, Agent, or Firm—Paul J. Koivuniemi; Gregory W. Steele; Lawrence T. Welch

[57] ABSTRACT

Provided are methods for determining whether a vaccinated animal is uninfected or infected with a virulent wild-type virus. Methods, vaccines and viruses are disclosed that are useful to seratologically distinguish infected from uninfected animals in populations of animals vaccinated with a properly incapacitated virus lacking an antigen of the wild-type virus.

1 Claim, No Drawings

OTHER PUBLICATIONS

Norid, B. and B. F. Vestergaard, "Immunoelectrophoretic Identification and Purification of Herpes Simplex Virus Antigens Released from Infected Cells in Tissue Culture", Intervirology 11:104–10(1979).

Khristova, V. et al., "Thymidine Kinase Activity of Virulent and Vaccinal Strains of Aujezsky's Disease Virus", Veterinary Science XXII(3):15–22.

G. Tatarov, "Apathogenic Mutant of the Aujeszky Virus Induced by 5-Iodo-2-Deoxyuridien (IUDR)", Zentralblatt Veterinarmedizin 15:847–53(1968).

Randall, R. E. et al., "Glycoproteins with Type Common and Type Specific Antigenic Sites Excreted from Cells Infected with Herpes Simplex Virus Types 1 and 2", J. Gen. Virol. 48:297–310 (1980).

VanZaane, D. et al., "Molecular-Biological Characterization of Marek's Disease Virus", Virology 121:116–32(1982).

Randall, R. E. and R. W. Honess, "Proteins of Herpesvirus Saimiri:Identification of Two Virus Polypeptides Released into the Culture Medium of Productively Infected Cells", J. Gen. Virol. 51:445–49(1980).

Ben-Porat, T. and A. S. Kaplan, "Synthesis of Proteins in Cells Infected with Herpesvirus", Virology 41:265–73(1970).

Rea, T. J. et al., "Mapping and Sequence of the Gene for the Pseudorabies Virus Glycoprotein Which Accummulates in the Medium of Infected Cells", J. of Virology 54(1):21–29(1985).

Gielkens, A. L. J. et al., "Genome Differences Among Field Isolates and Vaccine Strains of Pseudorabies Virus", J. Gen. Virol. 66:69–82(1985).

Lomniczi, B. et al., "Deletions in the Genomes of Pseudorabies Virus Vaccine Strains and Existence of Four Isomers of the Genomes", J. of Virology 49(3):970–79(1984).

Mettenleiter, T. C. et al., "Mapping of the Structural Gene of Pseudorabies Virus Glycoprotein A and Identification of Two Non-Glycosylated Precursor Polypeptides", J. of Virology of 53(1):52–57(1985).

Valenzuela, P. et al., "Antigen Engineering in Yeast:-Synthesis and Assembly of Hybrid Hepatitis B Surface Antigen-Herpes Simplex 1 gD Particles", Bio/Technology 3:323–26(1985).

Kieny, M. P. et al., "Expression of Rabies Virus Glycoprotein From a Recombinant Vaccinia Virus", Nature 312:163–66(1984).

Mettenleiter, T. C. et al., "Pseudorabies Virus Avirulent Strains Fail to Express a Major Glycoprotein", J. of Virology 56(1):307–11(1985).

Wathen, M. W. and L. M. K. Wathen, "Isolation, Characterization, and Physical Mapping of a Pseudorabies Virus Mutant Containing Antigenically Altered gp50", J. of Virology 51(1):57–62(1984).

Holland, T. C. et al., "Antigenic Variants of Herpes Simplex Virus Selected with Glycoprotein-Specific Monoclonal Antibodies", J. of Virology 45(2):672–82(1983).

Post, L. E. and B. Roizman, "A Generalized Technique for Deletion of Specific Genes in Large Genomes: αGene 22 of Herpes Simplex Virus 1 is Not Essential for Growth", Cell 25:227–32(1981).

Todd, D. and J. B. McFerran, "Control of Aujeszky's Disease", The Veterinary Record 117(24):647(1985).

Thomsen, D. R. et al., "Replication and Virulence of Pseudorabies Virus Mutants Lacking Glycoprotein gX", J. of Virology 61(1):229–32(1987).

Sandri-Goldin, R. M. et al., "Method for Induction of Mutations in Physically Defined Regions of the Herpes Simplex Virus Genome", J. of Virology 38(1):41–49(1981).

Quint, W. et al., "Construction and Characterization of Deletion Mutants of Pseudorabies Virus: A New Generation of 'Live' Vaccines", J. Gen. Virol. 68:523–34(1987).

METHOD OF DETECTING VIRAL INFECTION IN VACCINATED ANIMALS

CROSS-REFERENCE TO RELATED APPLICATIONS

This application is a divisional application of U.S. Pat. application Ser. No. 07/308,719, filed Feb. 9, 1989, now U.S. Pat. No. 5,128,128; which is a divisional application of U.S. Pat. application Ser. No. 07/049,865, filed Mar. 27, 1987, now U.S. Pat. No. 4,810,634 issued Mar. 7, 1989; which was the U.S. National Phase of PCT Patent Application No. PCT/US86/01322, filed Jun. 17, 1986; which was a continuation-in-part of U.S. Pat. application No. 06/760,130, filed Jul. 29, 1985, abandoned.

FIELD OF INVENTION

This invention relates to a serologically identifiable virus vaccine. The vaccine of the present invention allows one to distinguish between animals infected with a virulent wild-type virus, and those which have been vaccinated, by utilizing a serologically distinct virus for the vaccine.

BACKGROUND OF THE INVENTION

Pseudorabies virus (PRV) is a disease which infects many species of animals worldwide. PRV infections are variously called infectious Bulbar paralysis, Aujesky's disease, and mad itch. Infections are known in important domestic animals such as swine, cattle, dogs, cats, sheep, rats and mink. The host range is very broad and includes most mammals and, experimentally at least, many kinds of birds (for a detailed list of hosts, see D. P. Gustafson, "Pseudorabies", in Diseases of Swine, 5th ed., A. D. Leman et al., eds., (1981)). For most infected animals the disease is fatal. Adult swine and possibly rats, however, are not killed by the disease and are therefore carriers for the disease.

Populations of swine are particularly susceptible to PRV. Although the adult swine rarely show symptoms or die from the disease, piglets become acutely ill when infected and death usually ensues in 24 to 48 hours often without specific clinical signs (T. C. Jones and R. D. Hunt, Veterinary Pathology, 5th ed., Lea & Febiger (1983)).

PRV vaccines have been produced by a variety of techniques and vaccination in endemic areas of Europe has been practiced for more than 15 years. Losses have been reduced by vaccination, but vaccination has maintained the virus in the environment. No vaccine has been produced that will prevent infection. Vaccinated animals that are exposed to virulent virus survive the infection and then shed more virulent virus. Vaccinated animals may therefore harbor a latent infection that can flare up again. (See, D. P. Gustafson, supra).

Live attenuated and inactivated vaccines for PRV are available commercially in the United States and have been approved by the USDA (see, C. E. Aronson, ed., Veterinary Pharmaceuticals & Biologicals, (1983)).

Because adult swine are carriers of PRV, many states have instituted screening programs to detect infected animals. A problem arises in distinguishing between those animals carrying virulent PRV and those which have been vaccinated. The antigenic profiles of the virulent viruses and the viruses used in vaccines are the same and therefore it may be impossible to distinguish between infected and vaccinated animals. As a result, regulations concerning movement of seropositive swine would apply to both vaccinated swine and to swine that have been previously infected with PRV (C. E. Aronson, supra.).

PRV is a herpesvirus. The herpesviruses generally are among the most complex of animal viruses. Their genomes encode at least 50 virus specific proteins and contain upwards of 150,000 nucleotides. Among the most immunologically reactive proteins of herpesviruses are the glycoproteins found, among other places, in virion membranes and the membranes of infected cells. The literature on PRV glycoproteins refers to at least four viral glycoproteins (T. Ben-Porat and A. S. Kaplan, Virology, 41, pp 265-73 (1970); A. S. Kaplan and T. Ben-Porat, Proc. Natl. Acad. Sci. USA, 66, pp. 799-806 (1970)).

Several herpesviruses reportedly secrete glycoproteins into the medium of infected cells. Herpes simplex virus (HSV) releases glycoprotein C and several truncated forms of glycoprotein D into the medium (B. Norrild and B. F. Vestergaard, Intervirology, 11, pp. 104-10 (1979); R. E. Randall, et al., J. Gen. Virol., 48, pp. 297-310 (1980)). Marek's disease virus releases a considerable amount of the virion glycoprotein A into the medium (D. Van Zaane, et al., Virology, 121, pp. 116-32 (1982)); and herpes saimiri virus also releases a virion glycoprotein in the medium (R. E. Randall and R. W. Honess, J. Gen. Virol., 51, pp. 445-49 (1980)). PRV releases a glycoprotein into the medium which reportedly is not incorporated into the viral particles (T. Ben-Porat and A. S. Kaplan, Virology, 41, pp. 265-73 (1970); T. J. Rea, et al., J. Virol., 54, pp. 21-29 (1985)).

The PRV protein which is secreted into the medium has been referred to as 3a (T. Ben-Porat and A. S. Kaplan, supra), and is also referred to as glycoprotein X (gX) (T. J. Rea, et al., supra.). gX has the following characteristics when isolated from PRV-infected cells:

(1) it is the predominant protein in the culture medium of PRV infected animal cells in culture;

(2) it is a glycoprotein;

(3) it has a molecular weight of about 95 kd on SDS polyacrylamide gels;

(4) it is a sulfated protein;

(5) it is soluble in about 1% perchloric acid; and (6) it is immunogenic in standard laboratory mice.

The instant invention overcomes the problems referred to above, for example in screening swine for PRV infection, by providing a PRV strain which is immunologically distinct from the wild-type virus, thus allowing one to distinguish between vaccinated and infected animals without the need for sacrificing the tested animals.

These antigenic differences may be a result of deletion of one or more detectable antigenic polypeptides from the vaccine virus. As a result of these genetic changes, it is possible to immunologically distinguish between infected and vaccinated animals on the basis of their serological profiles without the need for sacrificing the tested animals.

INFORMATION DISCLOSURE

M. W. Wathen and L. K. Wathen, J. Virol., 51, pp.57-62 (1984) refers to a PRV containing a mutation in a viral glycoprotein (gp50) and a method for selecting the mutant utilizing neutralizing monoclonal antibody directed against gp50. Wathen and Wathen do not describe the use of this virus as a vaccine. Further, animals immunized with this virus would be serologically indistinguishable from infected animals.

T. C. Holland, et al., J. Virol., 45, pp. 672-82 (1983) refers to antigenic variants of HSV selected with glycoprotein-specific monoclonal antibodies. Included among the variants selected are two which fail to express HSV glycoprotein gC. Holland, et al. also do not teach or suggest the use of these variants for vaccines.

European patent publication 0 133 200 refers to a diagnostic antigenic factor to be used together with certain lectin-bound PRV glycoprotein subunit vaccines to distinguish carriers and noncarriers of PRV.

European patent publication 0 074 808 refers to specific DNA sequence insertions, deletions and substitutions in eukaryotic cell or viral genomes that are stably effected through the use of selectable DNA sequences comprising the herpesvirus thymidine kinase gene. Among the genomes listed as susceptible to manipulation is PRV. Another related publication also sets forth similar methods (L. E. Post and B. Roizman, "A Generalized Technique for Deletion of Specific Genes in Large Genomes: α Gene 22 of Herpes simplex Virus 1 Is Not Essential for Growth," Cell, 25, pp. 227-32 (1981)). The methods set forth in these documents are employed in producing the PRV of the present invention, infra.

A. J. M. Berns and A. L. J. Gielkens, European Publication No. 0 141 458 refers to deletion mutants of PRV. The deletions are not within a gene encoding a secreted glycoprotein. Furthermore Berns neither suggests or describes the use of such mutants to distinguish serologically between a vaccine and wild-type virus.

A. L. J. Gielkens, et al., "Genome Differences Among Field Isolates and Vaccine Strains of Pseudorabies Virus", J. Gen. Virol., 66, pp. 69-82 (1985) refers to comparing the genomes of different field isolates and modified live virus vaccine strains of pseudorabies virus (PRV) by BamHI restriction mapping. They reported observing two types of variations, (1) additions and/or deletions of nucleotide sequences to fragments derived from the $TR_S$ and $IR_S$ regions of the PRV genome, and (2) loss or gain of BamHI cleavage sites within the $U_L$ region of the genome. They speculate that analysis of viral DNA with restriction endonucleases may provide a method to distinguish PRV field strains.

We have determined that one of the PRV vaccines now commercially available contains a deletion for the gene encoding glycoprotein I as have Mettenleiter, et al., J. Virol., 56, pp. 307-11 (1985). We have also shown that another commercial strain (Bartha) lacks gp63. These vaccines may be useful in certain of the embodiments of the instant invention as described, infra.

B. Lomniczi, et al., "Deletions in the Genomes of Pseudorabies Virus Vaccine Strains and Existence of Four Isomers of the Genomes", J. Virol., 49, pp. 970-79 (1984) refers to characterization of two commercial vaccine strains of PRV (from Bartha and Norden) showing that they have deletions in the unique short sequence of the PRV genome between 0.855 and 0.882 map units. This area is within the BamHI 7 fragment of PRV. Nowhere do either of these documents describe or suggest a PRV lacking a secreted glycoprotein, a vaccine comprising such a mutant or a method of distinguishing between a vaccinated and infected animal by using such a PRV mutant.

U.S. Pat. No. 4,514,497 refers to PRV tk$^-$ deletions. It does not refer to PRV having deletions which allows one to serologically distinguish between animals infected with a virulent wild-type virus and those which are vaccinated.

SUMMARY OF THE INVENTION

As used herein, the expressions "properly incapacitated virus", and variants of that expression, and "avirulent", refer to both killed and attenuated viruses.

As used herein, "secreted glycoprotein" refers to a glycoprotein that accumulates in the medium of infected cells in culture.

The present invention relates to a vaccine comprising a properly incapacitated virus lacking at least one detectable antigen of the wild-type virus which allows the serological distinction between vaccinated and infected animals.

More particularly, the present invention relates to a pseudorabies virus lacking a serologically detectable polypeptide of the wild-type PRV.

More particularly, the present invention relates to a pseudorabies virus lacking a secreted glycoprotein of the wild-type PRV.

More particularly, the present invention relates to a pseudorabies virus lacking glycoprotein X.

The present invention also provides methods for distinguishing between vaccinated and infected animals and a multivalent vaccine comprising the above-described viruses and vaccines.

DETAILED DESCRIPTION OF THE INVENTION

The present invention relates to a vaccine which allows one to serologically distinguish between vaccinated and infected animals without the need for sacrificing the tested animals. The vaccine comprises a virus having a deletion for an antigenic polypeptide, particularly a secreted polypeptide, and more particularly a secreted glycoprotein.

We produced such a PRV by utilizing recombinant DNA techniques. Starting with a readily available plasmid (pPRXh1, also known as pUC1129) containing the gX gene that we wished to delete, together with another publicly available plasmid (pACYC184), we constructed a plasmid (pPRXK4) carrying the gX gene subcloned for convenient manipulation. We then removed the gX promoter from pPRXK4 and cloned it into another publicly available plasmid, pUC9, to construct plasmid pPGX1. Next, we removed the HSV thymidine kinase (tk) gene from plasmid pRB103 and inserted it into a site in pPGX1 so that it was fused to the gX promoter to produce plasmid pGXTK2. We then removed the BamHI 7 fragment of PRV containing the C-terminal coding region of the gX gene from pPRXh1 and inserted it downstream from the tk gene in pGXTK2 to form a plasmid (pGXTK3) in which the HSV tk gene is flanked by the PRV gX promoter and the C-terminal coding region for the gX gene. We next co-transfected rabbit skin cells with a tk$^-$ gX$^+$ PRV and pGXTK3 (tk$^+$ gX$^-$) to produce a tk$^+$ gX$^-$ PRV by the method of L. E. Post and B. Roizman, infra. Finally, we converted the tk$^+$ gX$^-$ PRV to a tk$^-$gX$^-$PRV to attenuate the virus for use as a vaccine. We have also demonstrated the efficacy of such a tk$^-$gX$^-$ PRV as a vaccine against pseudorabies disease.

Charts A-K are set forth to illustrate the constructions of the present invention. Certain conventions are used to illustrate plasmids and DNA fragments as follows:

(1) The single line figures represent both circular and linear double-stranded DNA.

(2) Asterisks (*) indicate that the molecule represented is circular. Lack of an asterisk indicates the molecule is linear.

(3) Endonuclease restriction sites are indicated above the line.

(4) Genes are indicated below the line.

(5) Distances between genes and restriction sites are not to scale. The drawings show their relative positions only.

The methods used in the plasmid constructions are standard recombinant DNA procedures, well known to those skilled in the art. These methods are described in, for example, T. Maniatis, et al., Molecular Cloning, Cold Spring Harbor Laboratory (1982) and B. Perbal, A Practical Guide to Molecular Cloning, John Wiley & Sons (1984), which are incorporated herein by reference.

Many of the specific methods employed herein are set forth in L. E. Post and B. Roizman, "A Generalized Technique for Deletion of Specific Genes in Large Genomes: α Gene 22 of Herpes simplex Virus 1 Is Not Essential for Growth," Cell, 25, pp. 227-32 (1981), which is incorporated herein by reference. In particular, the methods for co-transfection and selection procedures are found therein.

EXAMPLE 1

1. Construction of pPRXK4

Referring now to Chart A, we describe the construction of a plasmid for subcloning the complete gX gene.

Plasmid pPRXh1 (also known as pUC1129 and available as deposit No. B-15772 from the Northern Regional Research Laboratory, U.S. Department of Agriculture, Peoria, Ill.) which contains the gX gene and gX promoter from PRV, is digested with restriction endonucleases XhoI and KpnI. The third largest of the four fragments produced (fragment 1, about 2.6 kb) is isolated by polyacrylamide gel electrophoresis. Fragment 1 is blunt-ended with T4 DNA polymerase and EcoRI linkers are added.

Vector pACYC184 (available as deposit No. 37033 from the American Type Culture Collection, 12301 Parklawn Drive, Rockville, Md. 20852) is digested with EcoRI and treated with bacterial alkaline phosphatase (BAP) to yield fragment 2. EcoRI cuts the Cm$^r$ gene.

Fragments 1 and 2 are then ligated to produce plasmid pPRXK4. This plasmid contains the complete gX gene, including the likely gX promoter (see Rea, et al., supra).

2. Construction of pPGX1

Referring now to Chart B, we describe the subcloning of the gX promoter.

The nucleotide sequence recognized by restriction endonuclease MstI (TGCGCA) is located in the DNA sequence putatively encoding the 5'-untranslated region of the gX mRNA (Rea, et al., supra). pPRXK4 is digested with MstI and the second largest fragment (fragment 3, about 2.1 kb) is isolated. Fragment 3 is then cut with EcoRI, and the smaller piece (fragment 4, about 400 bp) is isolated. Plasmid pUC9 (available from Pharmacia P/L, Inc., Piscataway, N.J., USA) is digested with EcoRI and SmaI, and the larger fragment (fragment 5, about 2.6 kb) is isolated. Fragments 4 and 5 are then ligated at the EcoRI sites and by a MstI/SmaI fusion to produce pPGX1. This plasmid contains the gX promoter with a BamHI cleavage site immediately downstream from it.

3. Construction of pGXTK2

Referring now to Chart C, we describe the construction of a plasmid in which the gX promoter is fused with the HSV tk gene.

Plasmid pPGX1 from above is digested with BamHI and treated with BAP to yield fragment 6. Plasmid pRB103 contains the BamHI Q fragment from HSV-1 strain F (L. E. Post, et al., Proc. Natl. Acad. Sci. USA, 77, pp. 4201-05 (1980)). (Alternatively, plasmid pHSV106, which is commercially available from Bethesda Research Laboratories, Gaithersburg, Md., U.S.A., also contains the BamHI Q fragment and can be used in this construction.) pRB103 is digested with BamHI plus BglII and the second largest fragment (fragment 7, about 2.9 kb) is isolated. This fragment contains the HSV tk gene without its promoter. Ligation of the digested pPGX1 (fragment 6) with the fragment containing the tk gene (fragment 7) at the BamHI sites and by a BglII/BamHI fusion gives two plasmids containing the tk fragment in opposite orientations. The plasmid with the tk gene immediately downstream from the gX promoter is selected by examination of the BamHI plus EcoRI digestion patterns and is called pGXTK2.

4. Construction of pGXTK3

Referring now to Chart D, we describe a plasmid comprising the HSV tk gene and PRV sequences flanking it.

pPRXh1 (see 1, above) is digested with BamHI and fragment 8 (about 6.9 kb) is isolated. (This fragment is known in the literature as BamHI 7 (see Rea, et al., supra.)). pGXTK2 is digested with BamHI and treated with BAP to produce fragment 9. Fragment 8 is ligated into the BamHI site of pGXTK2 (fragment 9). The resulting plasmid with fragment 8 in the same orientation as the gX promoter is called pGXTK3. This plasmid has the tk gene immediately downstream from the gX promoter and replacing the DNA coding for the N-terminal amino acids of gX.

5. Co-transfection

Referring now to Chart E, pGXTK3 is cut with ClaI. The DNA fragment so produced which contains the C-terminal region of gX (effectively gX$^-$) and the entire HSV tk gene fused to the gX promoter is used to co-transfect rabbit skin cells together with DNA from a tk$^-$ gX$^+$ mutant of PRV (which we call PRV HR) which is selected by growth of PRV in the presence of iododeoxyuridine according to the method of Tatarov, Zentralblatt Veterinarmedizin, 15, pp. 847-53 (1968).

The tk$^+$ gX$^-$ recombinant viruses (which may be used for vaccine after proper incapacitation) are selected by growth in tk$^-$ human 143 cells (J. P. Weir, et al., Proc. Natl. Acad. Sci. USA, 79, pp. 1210-14 (1982); Panicali and Paoletti, Proc. Natl. Acad. Sci. USA, 79, pp. 4927-31 (1982); Campione-Piccardo, et al., J. Virol., 31, pp. 281-87 (1982); K. L. Poffenberger, et al., Proc. Natl. Acad. Sci. USA, 80, pp. 2690-94 (1983); M. F. Stinski, et al., J. Virol., 55, pp. 431-41 (1985)) in HAT medium (L. E. Post and B. Roizman, supra). We called the virus so produced PRV gX1 or DT-A. DT-A is tk$^+$ and is fully capable of killing mice.

Viruses selected for growth in HAT (e.g., DT-A) are analyzed for synthesis of gX by labeling viral proteins with $^{35}$S-methionine or $^{14}$C-glucosamine, followed by immunoprecipitation with anti-gX serum. No gX is detected.

Proteins from cells infected with the tk+ gX³¹ virus are also analyzed by western blots with anti-gX serum and no gX is detected in cells infected with the mutant virus.

It is also possible to remove the entire gX gene. For example, by digesting fragment 8 with NarI, one produces a fragment having the entire gX gene deleted (see Chart D). This fragment can then be employed in place of fragment 8 to produce a gX⁻ PRV entirely lacking the gX gene.

It has been known for some time that tk⁻ PRV are avirulent and make good vaccines. Therefore, to properly incapacitate DT-A to make a tk⁻ virus useful as a vaccine one could mutagenize and select for tk−PRV by the methods of Tatarov (see, e.g., G. Tatarov, "Apathogenic Mutant of the Aujeszky Virus Induced by 5-Iodo-2-Deoxyuridine (IUDR)", Zentralblatt Veterinarmedizin, 15, pp. 847–53 (1968); G. Tatarov, et al., "Investigation of Harmlessness and Immunogenicity of the MK Strain of Aujeszky's Virus", Vet. Nauki, 6, pp. 49–54 (1969); G. Tatarov, "Results of Use of Live Vaccine MK-25 Against Aujeszky's Disease", Vet. Sbirka, 7, pp. 10–12 (1974); G. Tatarov, "Bulgarian MK-25 Vaccine Against Aujeszky's Disease", Cah. Med. Vet., 43, pp. 347–52 (1974); G. Tatarov, et al., "Development of an Avirulent Mutant of Aujeszky's Disease Virus Under the Influence of 5-Bromo-Desoxyuridine", Veterinary Science, 18, pp. 3–12 (1981); V. Khristova, et al., "Thymidine Kinase Activity of Virulent and Vaccinal Strains of Aujezsky's Disease Virus", Veterinary Science, 22, pp. 15–22 (1985)); or by similar techniques (W. C. Topp, Virology, 113, pp. 408–11 (1981); S. Kit, et al., Exp. Cell Res., 31, pp.297–312 (1963); S. Kit et al., Virology, 130, pp.381–89 (1983)).

PRV▲gX1 which contains the HSV tk gene can also be converted to a tk− PRV by a recombinational event to remove the HSV tk gene by co-transfecting rabbit skin cells with this tk+ gX− PRV and a plasmid carrying a gX deletion, and selecting for tk− recombinants with araT according to the method of L. E. Post and B. Roizman, supra, as follows:

Referring now to Chart F, plasmid pPGX 1 was digested with BamHI and treated with BAP as set forth in Chart C, step (a) to produce fragment 6 comprising the gX promoter. Plasmid pPRXh1 is digested with BamHI to produce fragment 8 comprising the C-terminal coding region of gX as set forth above and in Chart D, step (a). This fragment is also known as the PRV BamHI 7 fragment. Fragments 6 and 8 are then ligated together, transformed into E. coli, and the clones are screened for the desired orientation of the BamHI 7 fragment by digestion with EcoRI plus PvuII. Proper orientation is indicated by the generation of 2.0 kb fragment by the digestion. The plasmid so produced is called p▲GXB7.

Plasmid p▲GXB7 is co-transfected with viral DNA from PRV▲gX1 using the calcium phosphate transfection technique (Mocarski, et al., Cell, 22:243 (1980)), into rabbit skin cells. The viruses that result from this transfection are plated onto vero cells in the presence of 100 μg/ml araT as described by Mocarski, et al., supra. Individual plaques are picked and analyzed for the desired tk− recombinant virus by restriction enzyme digestion of DNA as described in Mocarski, et al., supra. This virus is designated PRV GXTK−▲or DT-B (Chart G). These tk− PRV are useful attenuated viruses for vaccines as set forth in Example 2 below.

To differentiate between infected and vaccinated animals using these viruses, one could employ, for example, an ELISA assay. Generally, gX protein, produced, for example, in *E. coli* by recombinant DNA techniques (Rea, et al., supra.), is added to the wells of suitable plastic plates and allowed sufficient time to absorb to the plastic (overnight, 20°-25° C.). The plates are washed and a blocking agent (e.g.,BSA) is added to neutralize any unreacted sites on the plastic surface. A wash follows and then the pig serum is added to the wells. After about 1 hour incubation at 20°-25° C., the wells are washed and a protein A-horseradish peroxidase conjugate is added to each well for a 1 hour incubation at 20°-25° C. Another wash follows and the enzyme substrate (o-phenylenediamine) is added to the wells and the reaction is terminated with acid. Absorbance is measured at 492 nmeters to quantitate the amount of gX antibody present in the serum. Lack of gX antibody indicates that an animal is not infected. By testing for other antigens one can establish whether or not a given animal is vaccinated.

Although PRV▲GXTK− is an effective vaccine, the PRV tk− mutation selected by growth in iododeoxyuridine could be a point mutation. If it were a point mutation it could revert to tk+ and possibly be virulent. Therefore, a tk− PRV having a deletion is preferable. U.S. Pat. No. 4,514,497 refers to PRV tk− deletions. The marker rescue procedure used therein to make tk− PRV was first used to make tk− deletions in herpes simplex virus (J. R. Smiley, Nature, 285:333–35 (1980) and L. E. Post, et al., Cell, 24:555–65 (1981)).

Referring now to Chart H, the PRV tk− gene has been mapped to the BamHI 11 fragment of PRV (T. Ben-Porat, et al., Virology, 127:194–204 (1983)). The BamHI 11 fragment was isolated by agarose gel electrophoresis of BamHI-digested DNA from PRV Rice strain and cloned into pBR322 to produce plasmid pTK11. pTK11 has a single XhoI cleavage site within the tk gene. pTK11 was cut with XhoI and digested for various amounts of time with exonuclease Bal31, recircularized with ligase and transformed into *E. coli* DH1 (Maniatis, supra., p. 505). This produced a collection of plasmids with various deletions in the tk gene.

Two of these plasmids were selected, purified by CsCl density gradient centrifugation and sequenced by the method of Maxam and Gilbert, Methods in Enzymology, 65(part1), pp. 497–559 (1980). Plasmid p▲tk-3 had a deletion of 329 base pairs from within the tk gene and plasmid p▲tk-4 had a deletion of 275 base pairs.

Before the tk deletions could be crossed into the gX− viruses it was first necessary to make the viruses tk+ so the tk− deletion recombinants could be selected. PRV▲ GXTK− DNA was co-transfected with plasmid pTK11 into rabbit skin cells. The resulting recombinant viruses were isolated and grown in 143 cells in HAT medium to select a tk+ virus which we called PRV▲ gXtk+PRV. The DNA from this virus was then co-transfected with p▲tk-4 DNA into rabbit skin cells. The resulting viruses were plated on vero cells in the presence of araT to select for tk− recombinants. The resulting viruses were screened for the proper recombinant by preparation of DNA and restriction enzyme analysis. These recombinants had incorporated the tk deletion. One of these viruses, which we called PRV▲ gX▲tk or DT-C, contained the expected tk delection and a gX deletion. We determined that the LD50 of DT-C is greater than $10^7$ plaque forming units in mice. For comparison, the LD50 of PRV▲gXPRVTK+ was 3 pfu.

Although the particular embodiment described herein is directed to PRV and utilizes recombinant DNA techniques, it will be clear to those skilled in the art that similar vaccines containing delections for secreted glycoproteins can be produced by other techniques and utilizing other viruses, such as Marek's disease virus, and infectious bovine rhinotracheitis virus.

Although the disclosure herein relates primarily to PRV, the techniques employed herein may be used to produce serologically distinct herpesviruses in any situation where it is advantageous to distinguish between vaccinated and infected animals such as is the case with the PRV. Include, for example are Marek's disease virus and infectious bovine rhinotracheitis virus.

While we placed the HSV tk gene under the control of the gX promoter, the DNA fragment containing tk could be inserted so that it is under control of another PRV promoter, or any other promoter which could function for expression of the tk gene. For example, other HSV promoters, for example, the HSV ICP4 promoter, that can be expressed in PRV-infected cells could also be employed. For example, one could insert the PRV tk gene into the gX gene, or insert any other tk gene under the control of a promoter that can be expressed in PRV-infected cells.

While we used the tk gene as the marker gene insert, any marker gene could be inserted into the gX gene to inactivate it as long as the marker would allow selection of viruses carrying that marker from those that lack it. For example, antibiotic resistance genes could be used as the marker genes such as resistance to G418 or hygromycin.

It is also possible to insert genes other than a selectable marker into the gX gene. To construct such a virus, one could place the foreign gene into a plasmid such as pGXTK3, with the foreign gene replacing the tk sequences. This plasmid could then be co-transfected with DNA from the tk+ gX- virus illustrated in Chart E. Selection with araT will give recombinant viruses with the foreign gene inserted and expressed. Such a gene, for example, could encode an antigen of another type of virus, for example, transmissible gastroenteritis virus or porcine parvovirus, or a of a bacteria such as *E. coli*, which would then raise an immunogenic response against that other virus. In this embodiment of the invention one would therefore have produced a "multivalent" vaccine comprising antigens for two or more types of viruses or other pathogens.

As an example of the foregoing, we inserted the tissue plasminogen activator (tPA) gene into the gX gene as follows:

pPSA18 is a plasmid which contains the entire coding region for tPA, with a unique BamHI cleavage site in the 5'-untranslated region of the coding region. It is constructed as set forth in copending U.S. patent application Ser. No. 758,517, filed Jul. 26, 1985. Referring now to Chart I, pPSA18 is cut with BalI and BamHI linkers are added to produce fragment 11. Fragment 11 is then digested with BamHI to produce a 1.95 kb fragment (fragment 12) containing the entire coding region of tPA. Plasmid pPGX1 (Chart B) is then cut with BamHI to produce fragment 6. Fragments 12 and 6 are then ligated to produce plasmid pGXTPA. The proper orientation of the tPA cDNA with relation to the gX promoter is determined by digestion with EcoRI which produces a 1.1 kb fragment when the orientation is proper.

Referring now to Chart J, plasmid pGXTPA is digested with HindIII to produce fragment 13. The BamHI 7 fragment of PRV DNA is isolated as set forth above (fragment 8), and HindIII linkers are added to produce fragment 14. Fragments 13 and 14 are then ligated together to produce pGXTPA-B7. The proper orientation of the BamHI 7 fragment inserted into this plasmid is determined by digestion with EcoRI and SphI. A 5.8 kb fragment is produced thereby when the orientation is proper.

Plasmid pGXTPA-B7 is then co-transfected with viral DNA from PRV▲GX1 into rabbit skin cells. The resulting viruses are plated on vero cells in the presence of araT to select tk− recombinants. We called one of the viruses so selected PRV-GXTPA. When this virus infects cells, the cells produce and secrete tPA as detected by immunoprecipitation with anti=tPA antiserum. tPA activity of 20 ng/ml was detected by a fibrin solubilization assay (Unkeless, et al., J. Exp. Med., 137, pp. 85–111 (1973); Luskutoff, et al., Proc. Natl. Acad. Sci. U.S.A., 74, 3903–07 (1977)).

EXAMPLE 2

In this example we set forth the protection of mice and swine from PRV-induced mortality by vaccination with a thymidine kinase-deficient glycoprotein X deletion mutant (tk-gX-) of PRV.

1. Animals

Female CF-1 mice, 5–6 weeks old, were obtained from the Charles River Co.

Eighteen crossbred pigs, 5–6 weeks old and of mixed sex, were obtained from J. Gilmore Enterprises. Pigs were randomly allotted into three rooms, six pigs per room.

Pigs and mice were given non-medicated food and water ad libitum.

2. Viruses and Cells

PRV deletion mutants DT-A (HSVtk+gX−) and DT-B (tk−gX−) were constructed from the parental PRV (HR strain; tk−gX+) as set forth above. DT-B does not synthesize thymidine kinase and it does not synthesize gX due to deletion of the gX gene. The virulent PRV (Rice strain) was used as the challenge virus in all protection studies. Viruses were propagated in either Vero cells or porcine kidney-15 (PK-15) cells.

3. Microneutralization Assay

The microneutralization assay was done as described by T. C. Holland et al., J. Virol., 45, pp. 672–82 (1983). Mouse sera were incubated with virus and 10% rabbit complement for 3 hr at 37° C. while pig sera were incubated with virus in the absence of complement for 1 hr at 37° C. The neutralization titer was expressed as the reciprocal of the highest dilution of serum which protected greater than 50% of the cells from cytopathic effects.

4. Enzyme-linked Immunosorbent Assay (ELISA)

The antigen solution was prepared by diluting gX fusion protein (p60-11, produced as set forth in U.S. Pat. No. 5,041,370) to 20 μg/ml in Voller's buffer (50 mM $NaHCO_3$, 0.03% $NaN_3$, adjusted to pH 9.6 with NaOH). This was filtered through a 0.45 micron sterilizing filter (Sartorius SM 165 55 K). If needed, the filter solution was further diluted with Voller's buffer before use.

100 μl of p60-11 protein in Voller's buffer (concentration about 2 μg/ml) was added to each well of a 96 well plate (Costar 3590 EIA). Adsorption occurred during an overnight, room-temperature incubation. The wells were washed three times with 300 μl of Dulbecco's PBS (8 g/l NaCl, 0.2 g/l KCl, 0.2 g/l $KH_2PO_4$, and 1.14 g/l $Na_2HPO_4$; resultant pH was 7.3-7.4). Unreacted sites on the plastic surface were neutralized during a 2 hour 37° incubation with 3% BSA in Dulbecco's PBS (200 μl per well). A single wash of each well with 300 μl of Dulbecco's PBS followed. Then the adsorbed antigen was reacted with antibodies in 100 μl of diluted serum (obtained from pigs exposed to PRV) and incubated overnight at 4°. Unreacted antibodies were removed by three washes with Dulbecco's PBS (300 Ml/well). Then 100 Ml of Protein A-horseradish peroxidase conjugate (diluted 1/800 for mouse sera and 1/15,000 for pig sera; diluted in 50 mM Tris, 0.05% Tween-20, 1% BSA, 0.02% $NaN_3$, pH 8.0) was added to each well for a 2 hour, 37° incubation. Again, the wells were washed three times with Dulbecco's PBS (300 Ml/well). One hundred μl of substrate solution was added to each well. This solution was prepared by adding 10 mg of o-phenylenediamine (previously dissolved in 0.5 ml $CH_3OH$) and 25 μl of 30% (w/v) $H_2O_2$ to 49.5 ml buffer (17 mM Citric acid, 65 mM phosphate and 0.01% merthiolate adjusted to pH 6.3 with NaOH). The enzyme reaction continued for 10 minutes at room-temperature before 100 μl of 4.5M $H_2SO_4$ was added to each well. Absorbance of the chromophore was measured at 492 nmeters using a Titertek Multiskan.

5. Viral Isolation from Nasal Swabs

Nasal swabs collected from pigs were each placed in one ml of Eagles Basal Medium (BME; M.A. Bioproducts) supplemented with 3% fetal bovine serum (FBS) and antibiotics. Swabs were stored at −70° until they were assayed for the presence of virus. For the virus isolation assay, the nasal swabs in BME were thawed and the individual swabs were discarded. Samples (0.1 ml) were inoculated in duplicate onto porcine kidney-15 (PK-15; ATCC CCL33) cell monolayers and incubated for 1 hr at 37° to allow virus adsorption. An overlay of medium-199 (Flow Laboratories) supplemented with 4% FBS, antibiotics, and 1% agar was placed on the cell cultures. After 3 days the cell monolayers were stained with neutral red and the plaques were enumerated.

6. Experimental Design for the Mouse Study

The virulence of four PRV strains was evaluated in mice by determining the 50% lethal dose (LD50) of each strain. The four PRV strains were: 1) the wild-type (Rice strain), 2) DT-A, 3)DT-B, and 4)HR. Each virus strain was administered to either five or six groups of mice (10 mice/group) at various doses. Mice were inoculated with 50 μl of the respective viruses by the foot-pad route (Day 0). The LD50 determinations were made 14 days (Day 14) after administration of the viruses and sera were obtained from the surviving mice of groups given the highest dose of the respective viruses. The LD50 for each virus strain was calculated by the Spearman-Karber method.

Surviving mice from the LD50 virulence study were challenged intraperitoneally at day 14 with PRV Rice strain at approximately 10 times the LD50 (determined for the intraperitoneal route) for PRV Rice strain (10 LD50=$5.4\times10^2$pfu/mouse). The study was concluded 14 days after challenge (Day 28).

7. Experimental Design for the Swine Study

Pigs were injected intramuscularly on Day 0 with 2 ml of DT-B strain (about $1.5\times10^7$ pfu/pig), 2 ml of Norden live vaccine (PR-Vac) as recommended by the manufacturer, or saline. All pigs were challenged on Day 20 with about 40 LD50 of virulent PRV (Rice strain) (40 LD50=$1.1\times10^5$ pfu/pig). The study was terminated on Day 34.

Serum samples were obtained and each pig was weighed on Days 1, 20, and 34. Nasal swabs were taken daily on Days 19 through 34.

8. Criteria for Efficacy Evaluation

Efficacy of PRV DT-B strain ($tk^-gX^-$) as a vaccine was evaluated on the basis of protection against PRV-induced mortality and the ability to serologically distinguish between PRV DT-B-treated swine and swine exposed to field-type virus.

Table 1 shows the relative virulence of the four PRV strains in mice in terms of the respective LD50 determinations. DT-B and HR have greatly reduced virulence compared to the wild-type strain and DT-A, being at least 1000-fold less virulent.

Mice that survived the administration of the various PRV strains were subsequently challenged on day 14 by the intraperitoneal route with virulent wild-type PRV at a dose of 10 times the LD50 ($5.4\times10^2$ pfu/mouse). As shown in Table 2, mice given a dose of $1\times10^3$ pfu or greater of DT-B and mice given a dose of $2.3\times10^3$ pfu or greater of HR were protected from virulent wild-type PRV challenge. In addition, sera taken prior to challenge from mice given DT-B contained a high titer of neutralizing antibodies (neutralization titer=1024) while the reaction with gX antigenic determinants, based on the ELISA data, was relatively insignificant (ELISA absorbance=0.05). Sera taken prior to challenge from mice given HR contained a high titer of neutralizing antibodies (neutralization titer=2048) while the reaction with gX antigenic determinants was substantial (ELISA absorbance=0.60).

To evaluate the protective efficacy and diagnostic implications of PRV DT-B strain, swine were inoculated with DT-B, Norden live vaccine (PR-Vac) or saline by the intramuscular route on Day 0 and challenged intranasally with wild-type Rice strain on day 14. The results shown in Table 3 demonstrate that DT-B strain is comparable to Norden live vaccine (PR-Vac) in eliciting a significant neutralizing antibody response and affording protection from virulent Rice strain challenge. The data obtained from an ELISA using the gX fusion protein suggest that swine immunized with DT-B did not have antibodies against gX whereas sera taken from convalescent pigs that survived exposure to the wild-type Rice strain did. In this study sera taken from swine given Norden live vaccine (PR-Vac) did not react with gX antigenic determinants to a statistically significant extent ($P>0.05$), however, based on previous studies, swine given Norden live vaccine (PR-Vac) may form antibodies against gX because the Norden strain possesses the gene encoding gX. Therefore, sera taken from swine vaccinated with Norden live vaccine (PR-Vac) may vary in terms of reactivity with gX antigenic determinants.

Swine treated with DT-B and Norden live vaccine sporadically shed virus after challenge whereas saline-treated pigs shed virus continuously until death in most cases. No virus was detected in the nasal secretions of one pig treated with DT-B, and one pig treated with Norden live vaccine (PR-Vac). These results suggest that vaccinated pigs do not shed virus as readily as non-vaccinated pigs.

The average weight on Day 20 (prior to challenge) of pigs treated with DT-B was not significantly different (P>0.05) from the average weight of saline-treated control pigs, indicating that vaccination with DT-B did not adversely affect the growth of swine.

These results indicate that DT-B protects swine from virulent PRV challenge and allows the serological differentiation between vaccinated swine and convalescent swine previously exposed to virulent PRV. DT-B did not reduce the growth of treated swine. In addition, the virulence study in mice demonstrated that DT-B is less virulent than tk+ PRV strains in a species other than swine.

TABLE 1

| Virus Strain | Genetic Characteristics | MICE LD50 LD50 |
|---|---|---|
| Rice Strain | PRVtk$^+$gX$^+$ | 40 pfu/mouse |
| DT-A | HSVtk$^+$gX$^-$ | 34 pfu/mouse |
| DT-B | tk$^-$gX$^-$ | $9.4 \times 10^4$ pfu/mouse |
| HR | tk$^-$gX$^+$ | $>2.3 \times 10^6$ pfu/mouse |

TABLE 2

Protection of mice vaccinated with attenuated PRV strains

| Virus Strain | Genetic Characteristics | Dose (pfu/mouse) | Mortality After Challenge | Neutralization Titer[a] | ELISA absorbance[b] |
|---|---|---|---|---|---|
| DT-B | tk$^-$gX$^-$ | $1.0 \times 10^5$ | 0/6 | 1024 | 0.05 |
| | | $1.0 \times 10^4$ | 0/10 | | |
| | | $1.0 \times 10^3$ | 0/10 | | |
| | | $1.0 \times 10^2$ | 4/10 | | |
| | | $1.0 \times 10^1$ | 7/10 | | |
| | | $1.0 \times 10^0$ | 9/10 | | |
| HR | tk$^-$gX$^+$ | $2.3 \times 10^6$ | 0/10 | 2048 | 0.60 |
| | | $2.3 \times 10^5$ | 0/10 | | |
| | | $2.3 \times 10^4$ | 0/10 | | |
| | | $2.3 \times 10^3$ | 0/10 | | |
| | | $2.3 \times 10^2$ | 2/10 | | |
| Control | — | — | 10/10 | | 0.00 |

[a]Neutralization titer = reciprocal of the highest dilution of serum taken from survivors (prior to challenge with PRV Rice strain) that protected greater than 50% of cells from cytopathic effects.
[b]Absorbance values represent ELISA reactions obtained using a 1/10 dilution of serum. Sera were the same as used for the neutralization assay.

TABLE 3

Protection of swine vaccinated with attenuated PRV DT-B

| Preparation | Mortality | Geometric Mean Titer[b] | Arithmetic Mean of ELISA Absorbance[b] |
|---|---|---|---|
| DT-B | 0/6 | 91 | $0.072 \pm 0.016^e$ |
| PR-Vac | 0/6 | 36 | $0.130 \pm 0.061^e$ |
| Saline | 6/6 | <4[c] | $0.093 \pm 0.024$ |
| Rice[a] | — | — | $0.942 \pm 0.228^f$ |

[a]Five convalescent pigs that survived exposure to Rice strain were bled in a previous study. They are included here to provide gX reactive sera as a control used in the ELISA.
[b]Geometric mean titer is the geometric mean of the neutralization titers obtained for each of the six pigs in each group prior to challenge. Each neutralization titer is the reciprocal of the highest serum dilution that protected >50% of the cells from cytopathic effects.
[c]No detectable antibody.
[d]Arithmetic mean of ELISA absorbances is the arithmetic mean of the ELISA absorbance values (1/40 dilution of sera) obtained for sera taken from each of the 6 pigs/group prior to challenge, except the last value (see note a above).
[e]Not significantly different (P > 0.05; two-tailed Student's test) from saline-treated pigs.
[f]Significantly different (P < 0.05; two-tailed Student's test) from saline-treated pigs.

Example 3

Following essentially the same procedures as set forth in Example 2, we have also done similar experiments for the DT-C strain of PRV. DT-C has a deletion for the PRV tk gene and for that reason is the preferred embodiment of the present invention. The results of these experiments are set forth in tables 4-8. Tables 4 and 8 show the reduced virulence of DT-C in swine, sheep, and calves. Tables 5 and 6 show the protective ability of DT-C. Table 7 shows the dose titration for DT-C in swine.

TABLE 4

| Virus Strain | Genetic Characteristics | MICE LD50 LD50 |
|---|---|---|
| Rice Strain | PRVtk$^+$gX$^+$ | 9 pfu/mouse |
| DT-C | tk$^-$gX$^-$ | $>1.0 \times 10^7$ pfu/mouse |
| HR | tk$^-$gX$^+$ | $>1.5 \times 10^7$ pfu/mouse |

TABLE 5

Protection of mice vaccinated with attenuated PRV strains

| Virus Strain | Genetic Characteristics | Dose (pfu/mouse) | Mortality After Challenge | Neutralization Titer[a] | ELISA absorbance[b] |
|---|---|---|---|---|---|
| DT-C | tk$^-$gX$^-$ | $1.0 \times 10^7$ | 0/8 | 5120 | 0.051 |
| | | $1.0 \times 10^6$ | 0/8 | | |
| | | $1.0 \times 10^5$ | 0/8 | | |
| | | $1.0 \times 10^4$ | 0/8 | | |
| | | $1.0 \times 10^3$ | 0/8 | | |
| | | $1.0 \times 10^2$ | 2/7 | | |
| | | $1.0 \times 10^1$ | 7/8 | | |
| HR | tk$^-$gX$^+$ | $1.5 \times 10^7$ | 0/6 | 2560 | 0.974 |
| | | $1.5 \times 10^6$ | 0/7 | | |
| | | $1.5 \times 10^5$ | 0/8 | | |
| | | $1.5 \times 10^4$ | 0/8 | | |
| | | $1.5 \times 10^3$ | 0/8 | | |
| | | $1.5 \times 10^2$ | 3/8 | | |
| | | $1.5 \times 10^1$ | 5/8 | | |
| Control | — | — | 7/8 | <20 | 0.000 |

[a]Neutralization titer = reciprocal of the highest dilution of serum taken from survivors (prior to challenge with PRV Rice strain) that protected greater than 50% of cells from cytopathic effects.
[b]Absorbance values represent ELISA reactions obtained using a 1/10 dilution of serum. Sera were the same as used for the neutralization assay.

TABLE 6

Protection of swine vaccinated with attenuated PRV DT-C

| Preparation[a] | Mortality | Geometric Mean Titer[b] | Arithmetic Mean of ELISA Absorbance[c] |
|---|---|---|---|
| DT-C | 0/6 | 26 | 0.072[d] 0.388[e] |
| PR-Vac | 0/6 | 16 | 0.105[e] 0.645[e] |
| BME | 3/6 | <8 | 0.059[d] 0.250[e] |

[a]Pigs receiving DT-C, PR-Vac, and BME had weight gains from 8.1 to 27.1, 6.5 to 23.0, and 6.0 to 11.4 kg respectively for survivors from day 0 to day 35 of the test.
[b]Geometric mean of the neutralization titers obtained for each of the six pigs in each group prior to challenge. Each neutralization titer is the reciprocal of the highest serum dilution that protected >50% of the cells from cytopathic effects.
[c]Arithmetic mean of the ELISA absorbance values (1/40 dilution of sera) obtained for sera taken from each of the 6 pigs/group prior to challenge. Means with different superscripts were significantly different (P < 0.05) from the day 20, BME (Eagle's basal medium) control value. First No. is pre-challenge, second No. is post-challenge.

TABLE 7

Dose Titration of DT-C in Swine

| Dose (pfu/pig) | Mortality[a] (Rice Challenge) | Geometric Mean Titer[b] |
|---|---|---|
| $1 \times 10^7$ | 0/6 | 23 |
| $1 \times 10^6$ | 0/6 | 25 |
| $1 \times 10^5$ | 0/6 | 18 |
| $1 \times 10^4$ | 0/6 | 18 |
| $1 \times 10^3$ | 0/6 | 18 |
| $1 \times 10^2$ | 0/6 | 20 |
| Control | 5/6 | <4 |

[a]Swine were administered 2 ml of each preparation at the indicated dosage by intramuscular injection on day 0 and were challenged on day 21 with about 80 LD50 ($2.2 \times 10^5$ pfu/pig) of PRV Rice strain.
[b]See note b, Table 6.

TABLE 8

Virulence of DT-C for Sheep and Calves

| Animal | Inoculum (pfu/animal) | Route[a] | Dead/Tested | Positive Nasal swabs[b] |
|---|---|---|---|---|
| sheep | 4 × 10⁷ | intranasal | 1/3[c] | 0/3 |
|  | 4 × 10⁷ | intramuscular | 0/3 | 0/3 |
| calves | 4 × 10⁷ | intranasal | 0/3 | 0/3 |
|  | 4 × 10⁷ | intramuscular | 0/3 | 0/3 |

[a] The virus suspension was administered in a total volume of 2 ml by the intranasal (1 ml per nostril) or intramuscular routes. Animals were observed for symptoms of Aujeskey's disease for 21 days post-administration.
[b] Swabs of the nasal mucosa were taken from each animal at termination of the experiment and these were tested for PRV as described above.
[c] One sheep died on day 14 exhibiting no symptoms of Aujeskey's disease or viral shedding. The probable cause of death in this animal was coccidiosis. This disease was diagnosed in other sheep in both groups.

In another aspect of the present invention, to ensure that a gX⁻tk⁺ virulent PRV does not result from a theoretically possible recombination between the gX⁻tk⁻ PRV of the present invention and a wild-type PRV in the field, the gX⁻tk⁻PRV is further engineered. By following the general methods set forth above a deletion is made in the PRV gp50 gene at its original locus and a copy of the gp50 gene is inserted into close linkage, or inserted within, the tk gene. To delete the original gp50 gene, one can employ the PvuII/BamHI fragment of fragment 8 (see Chart D) to perform a marker rescue experiment as set forth above. The product virus will be gX⁻tk⁻ and have a copy of the gp50 gene closely linked to, or within what remains of the tk gene sequence. Since gp50 is essential to the virus viability, any gX⁻ virus resulting from a recombination would also be gp50⁻ and nonviable. Therefore, it will be impossible to separate the gX⁻ and tk⁻ deletions by recombination in the field to produce a virulent gX⁻ PRV.

In more detail, referring now to Chart K, p▲TK-4 from above is digested with SphI and BamHI to produce a fragment containing the tk deletion, and the fragment is then isolated. pUC19 (available from Pharmacia/PL) is digested with BamHI and SphI and the larger fragment so produced is isolated. These two fragments are then ligated to produce plasmid pUC▲TK4-V which contains a single SalI site adjacent to the tk deletion. pUC▲TK4-V is then cut with SalI and the ends made blunt with T4 DNA polymerase to produce plasmid p▲TK4gp50-8.

Plasmid p▲TK4gp50-8 is cut with HindIII, and then NdeI, which cuts between the gX and gp50 genes, and StuI, which cuts within the gp63 gene, to produce a NdeI/StuI fragment containing the gp50 gene (fragment B, about 1.8 kb). This is filled in with T4 DNA polymerase and then fragments A and B are ligated to produce plasmid p TK4gp50-8.

Plasmid p TK4gp50-8 is cut with HindIII, and then co-transfected with PRV DNA into rabbit skin cells. The resulting virus are grown on a selective medium containing araT to isolate tk⁻ recombinants having the structure shown in Chart K (c). We called this virus PRV▲TKgp50.

PRV▲TKgp50 is then co-transfected with pGXTK3 from above, and tk⁺ viruses are selected on 143 cells in HAT medium. This virus, called PRV▲TKgp50tk⁺ (HSV), is gX⁻.

Next, the PvuII/BamHI fragment containing the gp63 and gI genes made by digesting BamHI 7 with these enzymes is subcloned into the PvuII/BamHI fragment of pBR322 to produce plasmid pPR28-1 (see copending U.S. patent application Ser. No. 844,113, filed Mar. 26, 1986). Plasmid pPR28-1 is cut with PvuII, BamHI linkers are added, and the fragment so produced is digested with BamHI to convert the 5 kb PvuII/BamHI fragment into a BamHI fragment. This BamHI fragment is then cloned into the BamHI site of pPGX1 (produced above). The resulting plasmid is co-transfected with PRV▲TKgp50tk⁺(HSV). The resulting viruses are selected for the tk⁻ phenotype by growth on araT. The selected viruses have the gp50 gene inserted into the remaining portion of the tk gene as well as deleted from its normal locus. They are also gX⁻. Therefore, any recombination with a field virus that gives a tk⁺gX⁻ virus would produce a virus that lacks a gp50 gene. Since gp50 is an essential gene, such a virus would be non-viable.

Although our example relates to PRV, it should be clear to those skilled in the art the same technique is useful to produce similar recombination-proof vaccine viruses in other herpesviruses. In general, the steps include 1) insertion of an essential gene adjacent to a mutation conferring avirulence, and 2) deletion of that essential gene from its normal locus, which is linked to the deleted gene for a secreted protein. Even more generally, moving essential genes from their normal positions will reduce the probability of recombination with wild-type viruses.

Insertion of a selectable marker is not absolutely required to construct a PRV lacking gX. For example, a plasmid containing a deletion in the gX coding region can be made by deleting the base pair BamHI fragment from within the gX gene. This plasmid is then be co-transfected with PRV DNA followed by screening the viruses derived from that transfection for either lack of the deleted piece of DNA by nucleic acid hybridization, or by screening for lack of gX by an antibody screen (Holland, et al., J. Virol., 46, pp. 649–52 (1983)).

The polypeptide (e.g., gX⁻) deletion viruses employed in the vaccines of the present invention can also be produced by other techniques of inducing mutations followed by screening for viruses lacking the polypeptide (e.g., gX) or any other technique which is used to produce a virus that has a deletion which renders the vaccine virus serologically distinct from the wildtype virus. For example, although one could not select gX⁻ PRV (anti-gX antibodies do not neutralize PRV) one can use the method of T. C. Holland, et al., supra., to select for gI or gIII (Wathen, J. Virol., 58, 173–78 (1986)) deletions in PRV which are useful in the vaccines of the present invention.

While attenuation by inactivating or deleting the tk gene (Tatarov, supra.; Post and Roizman, supra.) is the preferred method, the gX⁻ viruses of the instant invention may be subjected to conventional chemical or physical inactivation procedures whereby the virus is rendered nonvirulent but still retains its antigenic properties. These inactivated vaccines may be formulated with a suitable adjuvant, e.g., alum. For a general description of various vaccine preparation techniques see J. I. Duffy, Vaccine Preparation Techniques, Noyes Data Corporation (1980), and G. W. Warr, "Preparation of Antigens and Principles of Immunization", in J. J. Marchalonis and G. W. Warr, eds., Antibody As A Tool-The Applications Of Immunochemistry, pp. 21–58, John Wiley & Sons (1982).

The virulent PRV virus may be propagated in animal tissue cultures until the virus is rendered nonpathogenic, i.e., avirulent. PRV can be propagated in a wide variety of tissue culture systems including, for example, chick embryo, duck embryo, porcine kidney, porcine testes, embryonic bovine kidney, feline kidney, canine kidney and monkey kidney; and also in established cell lines, such as, for example, Madin Darby bovine kidney (MDBK), and Madin Darby canine kidney (MDCK).

Attenuation of PRV may be accomplished by standard serial passages including terminal dilution passage techniques wherein a sufficient number of passages in a susceptible tissue culture is employed until the virus is rendered nonpathogenic without loss of immunogenicity.

The passage time intervals should be such as to s

CHART C.
Construction of pGXTK2

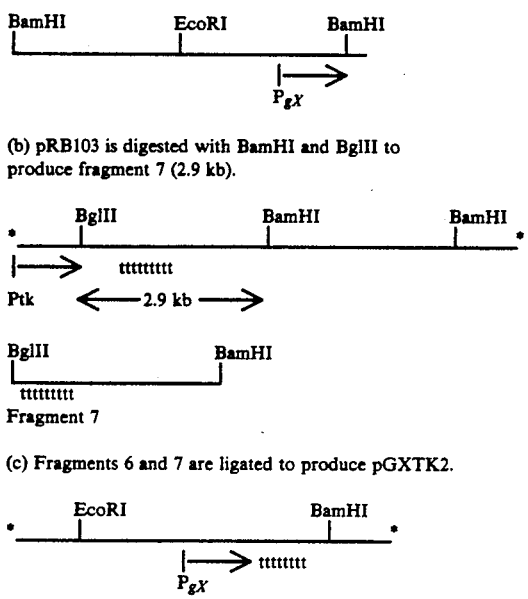

(b) pRB103 is digested with BamHI and BglII to produce fragment 7 (2.9 kb).

(c) Fragments 6 and 7 are ligated to produce pGXTK2.

$P_{tk}$ = thymidine kinase promoter
t = thymidine kinase gene

CHART D.
Construction of pGXTK3

(a) pPRXh1 is digested with BamHI to produce fragment 8 (6.9 kb).

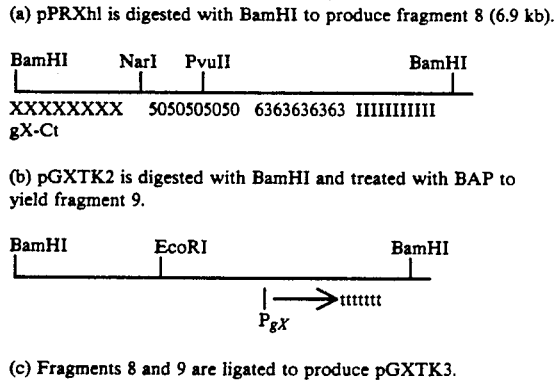

(b) pGXTK2 is digested with BamHI and treated with BAP to yield fragment 9.

(c) Fragments 8 and 9 are ligated to produce pGXTK3.

gX-Ct = C-terminal coding region of gX gene
50 = glycoprotein 50 gene
63 = glycoprotein 63 gene
I = glycoprotein I gene

CHART E.
Co-transfection with pGXTK3 and a tk⁻PRV.

(a) Co-transfection of pGXTK3 and a tk⁻gX-PRV produces the tk⁺gX⁻ product PRV▲gX1 (or DT-A).

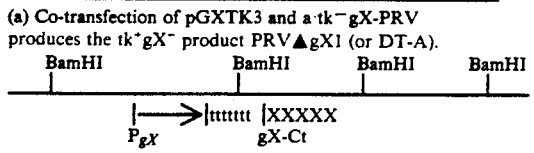

CHART F.
Construction of p▲GXB7

(a) pPGX1 is digested with BamH1 and treated with BAP to yield fragment 6.

(b) pPRXh1 is digested with BamHI to produce fragment 8 (6.9 kb).

(c) Fragments 6 and 8 are ligated to produce plasmid p▲GXB7.

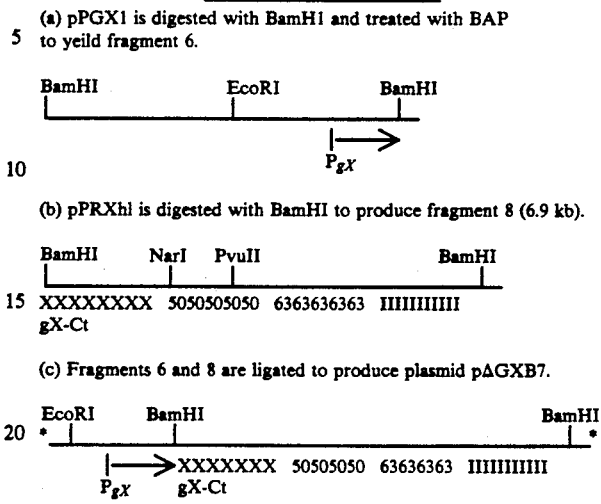

CHART G.
Construction of PRV▲GXTK⁻ by recombination (a) Co-transfection of PRV▲GX1 and p▲GXB7 and recombination produces PRV▲GXTK⁻.

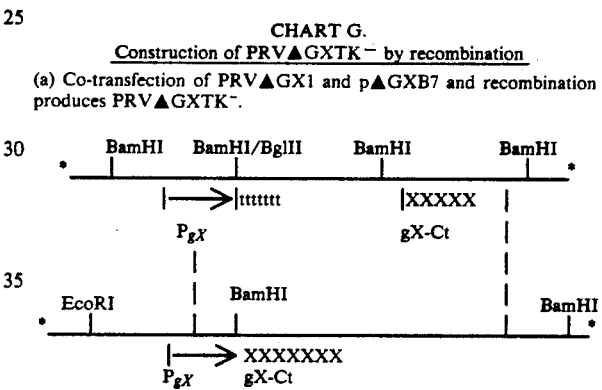

| = region of crossover (scale of right hand crossover region is extremely distorted)

CHART H.
Construction of tk deletion plasmids (a) BamHI 11 is cloned into pBR322 to produce plasmid pTK11.

(b) pTK11 is digested with XhoI to produce fragment 10.

(c) Fragment 10 is digested with Bal31 and then recircularized to produce plasmids, e.g., pΔtk-3 and pΔtk-4, having varying length deletions in the tk gene.

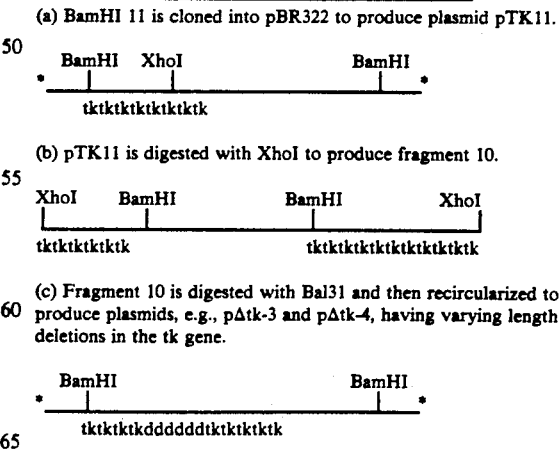

tk = thymidine kinase gene
d = deletion in the thymidine kinase gene

CHART I.
Construction of pGXTPA (a) Plasmid pPSA18 is cut with BalI and BamHI linkers are added to produce fragment 11.

pPSA18:

Fragment 11:
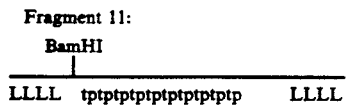

(b) Fragment 11 is digested with BamHI to produce fragment 12 (1.95 kb).

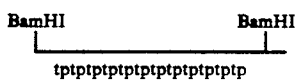

(c) Plasmid pPGX1 (Chart B) is cut with BamHI to produce fragment 6.

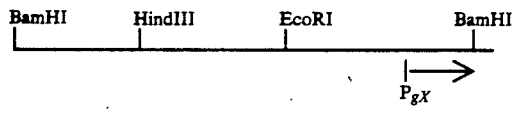

(d) Fragments 6 and 12 are ligated to produce plasmid pGXTPA.

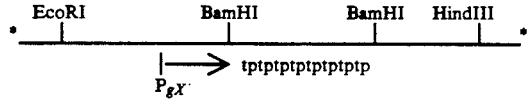

tp = tissue plasminogen activator gene
L = BamHI linkers

CHART J.
Construction of plasmid pGXTPA-B7.

(a) Plasmid pGXTPA is digested with HindIII to produce fragment 13.

-continued
CHART J.
Construction of plasmid pGXTPA-B7.

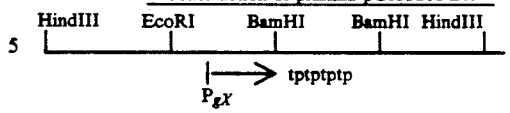

(b) HindIII linkers are added to fragment 8 (Chart D) to produce fragment 14.

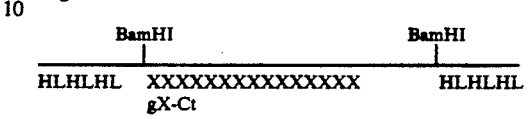

(c) Fragments 13 and 14 are then ligated together to produce pGXTPA-B7.

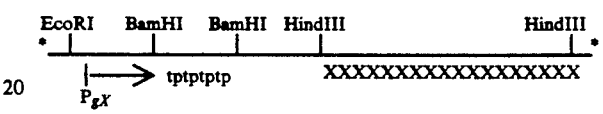

HL = HindIII linkers

CHART K.
Production of recombination-proof viruses.

(a) pΔTK-4

(b) BamHI 7

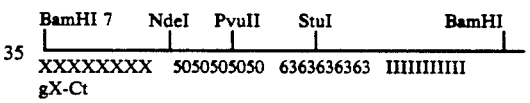

(c) PRVΔTKgp50

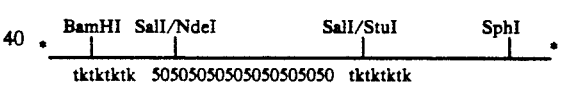

I claim:

1. A method for determining whether an animal, vaccinated with a vaccine which comprises an avirulent pseudorabies virus that fails to produce glycoprotein X, has been infected with a virulent wild-type pseudorabies virus comprising detecting the presence or absence of antibodies specific for glycoprotein X in serum from the vaccinated animal.

* * * * *

UNITED STATES PATENT AND TRADEMARK OFFICE
CERTIFICATE OF CORRECTION

PATENT NO. : 5,275,934            Page 1 of 2
DATED       : January 4, 1994
INVENTOR(S) : Leonard E. Post, et al It is certified that error appears in the above-indentified patent and that said Letters Patent is hereby corrected as shown below:

On the title page, item [60] Related U.S. Application Data, "Ser. No. 318,719,"

Column 3, line 42, "and $IR_8$"

Column 6, line 62, "PRV gX1"

Column 7, line 1, "$gX^{31}$"

Column 7, line 66, "PRV GXTK-▲or"

Column 13, line 59, "Student's test"

Column 13, line 61, "Student's test"

Column 15, line 46, "produce plasmid p▲TK4gp50-8."

Column 15, line 47, "Plasmid p▲TK4gp50-8 is cut with HindIII, and then"

UNITED STATES PATENT AND TRADEMARK OFFICE
CERTIFICATE OF CORRECTION

PATENT NO. : 5,275,934
DATED : January 4, 1994
INVENTOR(S) : Leonard E. Post, et al It is certified that error appears in the above-indentified patent and that said Letters Patent is hereby corrected as shown below:

Column 15, line 53, "p TK4gp50-8."

Column 15, line 54, "p TK4gp50-8"

Signed and Sealed this

Twenty-ninth Day of November, 1994

Attest:

BRUCE LEHMAN

*Attesting Officer*     *Commissioner of Patents and Trademarks*